United States Patent
Miller

(10) Patent No.: US 6,997,711 B2
(45) Date of Patent: Feb. 14, 2006

(54) DENTAL IMPLANT

(76) Inventor: Robert Jeffrey Miller, 7799 Talavera Pl., Del Ray Beach, FL (US) 33446

( * ) Notice: Subject to any disclaimer, the term of this patent is extended or adjusted under 35 U.S.C. 154(b) by 282 days.

(21) Appl. No.: 10/328,824

(22) Filed: Dec. 23, 2002

(65) Prior Publication Data

US 2004/0121289 A1 Jun. 24, 2004

(51) Int. Cl.
*A61C 13/12* (2006.01)
(52) U.S. Cl. .................................. 433/174; 433/172
(58) Field of Classification Search ............... 433/172, 433/173, 174, 175, 176, 221, 225; 600/231, 600/232, 233, 235, 201
See application file for complete search history.

(56) References Cited

U.S. PATENT DOCUMENTS

| | | | |
|---|---|---|---|
| 4,468,200 A | 8/1984 | Munch | |
| 4,626,214 A | 12/1986 | Artal | |
| 4,713,004 A | 12/1987 | Linkow et al. | |
| 5,061,181 A | 10/1991 | Niznick | |
| 5,199,873 A | 4/1993 | Schulte et al. | |
| 5,344,457 A | 9/1994 | Pilliar et al. | |
| 5,639,237 A | 6/1997 | Fontenot | |
| 5,823,777 A | 10/1998 | Misch et al. | |
| 5,897,319 A * | 4/1999 | Wagner et al. | 433/174 |
| 5,989,028 A | 11/1999 | Niznick | |
| 6,048,204 A | 4/2000 | Klardie et al. | |
| 6,149,432 A | 11/2000 | Shaw et al. | |
| 6,234,797 B1 | 5/2001 | Ura | |
| RE37,646 E | 4/2002 | Zuest | |
| 6,375,465 B1 | 4/2002 | Engman et al. | |
| 6,379,153 B1 | 4/2002 | Schroering | |
| 6,402,515 B1 | 6/2002 | Palti et al. | |
| 6,413,089 B1 | 7/2002 | Ashman et al. | |
| 6,464,500 B1 | 10/2002 | Popovic | |

FOREIGN PATENT DOCUMENTS

| | | |
|---|---|---|
| EP | 1145691 A1 | 10/2001 |
| WO | WO 94/25637 A1 | 11/1994 |
| WO | WO 02/060507 A1 | 8/2002 |

OTHER PUBLICATIONS

Friatec AG Brochure, L'alternativa per la Migliore Protesi, 3 pages.
Philippe D. Ledermann et al., II Concetto Ha-Ti, Schweiz Monatsschr Zahnmed, vol. 101, May 1991.
Dossier Anatomia Patologica Brochure, Dental Cadmos, Jun. 1994, 2 pages.
Lifecore Biomedical, Inc. Brochure, Sustain Dental Implant System, 2 pages.
Intec Catalog & Owners Manual, 4th Edition, Hexed-Head Implant System, 20 pages.

\* cited by examiner

*Primary Examiner*—Cary E. O'Connor
*Assistant Examiner*—Candice C. Stokes
(74) *Attorney, Agent, or Firm*—Greenberg Traurig LLP

(57) ABSTRACT

The dental implant includes a body with a coronal end and an apical end. The implant intraosseous region includes a tapered thread which has a constant depth on an apical edge. A coronal edge to the thread varies in profile. There is equal spacing between the apical end and the coronal end of the implant. The coronal edge varies in profile, and can have a profile formed of two or three components. There is at least two cutting actions of the thread to permit for effective implantation in the bone without leading to microfracture.

72 Claims, 4 Drawing Sheets

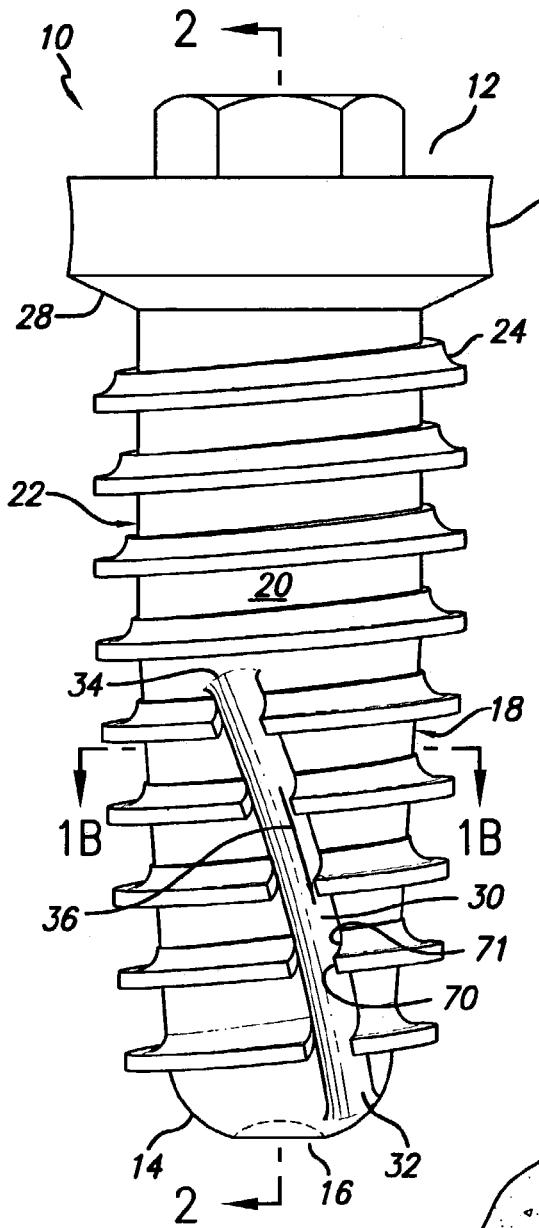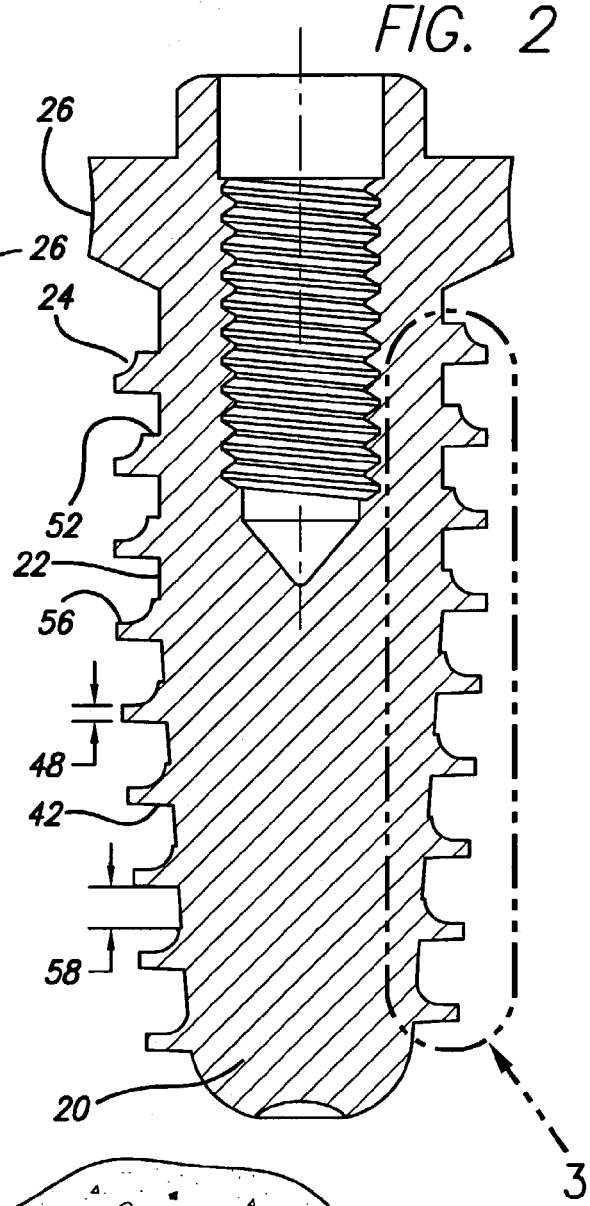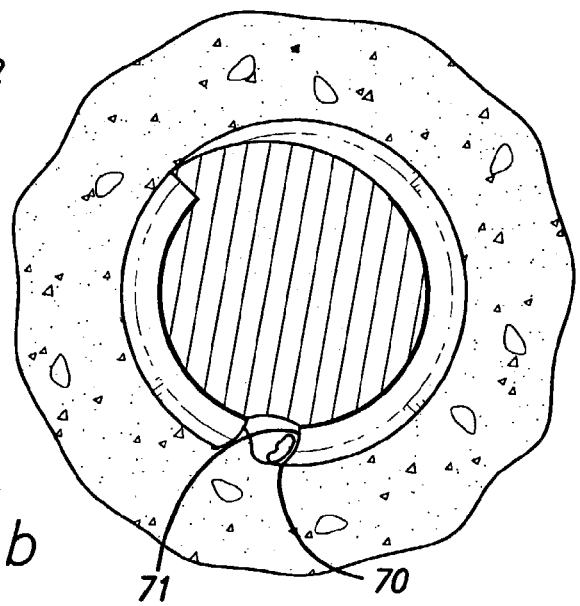

DENTAL IMPLANT

BACKGROUND OF THE INVENTION

This invention relates to dental implants. In particular it is concerned with a threaded dental implant with an improved thread profile.

Many different kinds of thread patterns are known for dental implants. These patterns can vary from constant pitch and size to a variable profile thread. As implants have developed from a relatively smooth surfaced machined titanium to a more roughened surface to enhance bone apposition there has developed a reductive process as the implant is turned through the bone. This reductive process has lead to a less intimate contact of the implant body to the bone. This in turn leads to a less stable interface for early or immediate loading of the implant.

Compensation for this reduction in contact, has resulted in implants employing osteocompressive designs to stabilize the implant body in the bone. The known osteocompressive designs, however, may result in microfracture of the bone leading to greater bone turnover and early reduction in stress-bearing bone.

It is an object of the present invention to provide a dental implant with an appropriate thread to minimize the disadvantages of known designs and provide for an implant permitting for early loading of the implant. Early loading of the implant has advantages for patients and all associated with the dental implant process since less time is needed to provide for implantation, healing and effective use of the implant in the patient's jaw.

The implant of the present invention seeks to further enhanced stability of the implant in the bone which varies in density in different regions of the individual.

SUMMARY OF THE INVENTION

According to the invention there is provided a dental implant having a radial compression threading that results in a thread pattern that maintains a cutting edge substantially along the entire thread length.

In a further preferred form the coronal radius of the thread moves mediolaterally to compensate for the reductive process while not over compressing bone. This leads to a more intimate contact of the implant and the bone while minimizing microfracture and thereby allowing early or immediate loading with a higher probably of osseointegration.

According to the invention, the implant includes a body, a coronal end of the body, an apical end of the body, and a helical thread extending along the face region of the body from a position towards the apical end to a position towards the coronal end of the body.

Each thread has an apical side and a coronal side, and the width between the apical side and the coronal side is substantially constant and the width of the thread on the apical side is also substantially constant. On the coronal side the thread pattern varies and changes progressively preferably from the apical end towards the coronal end.

On the coronal side of each thread the depth includes a first relatively flat portion, a radial portion and a further extended second flat portion. The further second extended flat portion meets with the edge of each thread. In some preferred forms of the invention, the final thread near or adjacent to the coronal end is such that the first flat portion occupies about 50% of the overall depth of the thread. In some other preferred forms of the invention this percentage may be different and may be about 100% of the depth.

The edge of each thread has a depth which is substantially constant and provides a first cutting edge or surface. The interface between the first flat portion of the coronal side and the curved portion provides a second cutting edge or surface. The threads have a depth being the distance between the body region and the outer edge of the thread. The threads also have a width, the width being the distance between the apical end and the coronal end of each thread. Each thread ends in an edge and the width of each thread is substantially the same between the apical end and the coronal end of the implant.

There is a space between each thread, the space being the distance between the coronal end of a first thread and the apical end of an adjacent thread. The space is substantially the same between the majority of the threads in the implant.

As the first flat portion of the coronal side extends in depth from the face region of the body, the further coronal second flat side decreases. Preferably at a position substantially adjacent to the coronal end of the body, the further coronal edge may be substantially minimal or zero.

In the preferred form of the invention the overall width of each thread is substantially the same and the spacing between the top of the coronal edge and the bottom of the apical edge of each adjacent thread is substantially constant. Likewise, the depth of the first cutting edge of each thread is substantially constant.

By having at least two cutting areas for the thread the dental implant tends to prevent a shearing action on the bone as the implant is screwed into position on the bone.

In yet a further preferred form of the invention the apical side of the thread has a relatively small rise from the horizontal. Preferably this rise from the horizontal is about 3 degrees and can be in a range of about 2 to 10 degrees. The first and second flat portions of coronal side of the thread are substantially horizontal. In some forms of the invention there may be an angular offset relative to the horizontal of the first or second flat portions of the coronal edges of the thread.

In a preferred form of the invention the construction of the preferred form of the thread of the implant is such as to maintain stability of the implant by counter-balancing the reductive nature of the roughened surface as the implant is turned through the bone. One or both of the cutting areas are maintained in contact with bone essentially through the entire thread pattern bone interface. This preferably maintains an inter-thread bone which does not compromises stability. Since there is essentially no compressed inter-thread bone the likelihood of microfracture is decreased and bone strength is maintained.

This is achieved by having dual cutting threads with variable compression with a variable compression thread surface. This is effectively achieved by having the width of the threads substantially constant to the outer edge, and thereby having the outer cutting edge substantially constant in its depth, and having the depth of the thread substantially constant between the apical end and the coronal end. The coronal surface of the thread varies in profile between the apical end and the coronal end.

Preferably there is an increasing depth of the first flat portion from the body region in a direction from the apical end to the coronal end and as that depth increases adjacent to the body region, the second flat portion of the coronal side progressively decreases.

In yet a further preferred form of the invention the thread body contains a spiral vent for creating a self-tapping ability, the spiral vent is directed in a manner such that bone chips move towards the apical end as the implant is threaded into the bone. The apical end of the implant is an area of decreased bone density. The apical end of the implant preferably contains an involution for permitting the implant to seat effectively in the presence of bone chips without excessive hydraulic pressure and osteocompression.

The spiral vent is essentially self-tapping and there is a positive rake angle with the vent thereby minimizing microfracture of the bone. The spiral vent extends circumferentially about one-quarter of the circumference of the body and extends in length for about one-half of the implant length. The output or outlet from the spiral vent is directed towards the apical bent or involution.

Towards the coronal end of the implant after the termination of the thread, there is an angled segment of wider depth than the thread portion, the angled segment is beveled to prevent tissue down growth along the implant body, allow for transmucosal attachment and sealing of the implant osteotomy. Between the angled bevel and the coronal end, there is a concave shaped transmucosal polished collar, such collar permitting for circumferential gingival fibers to surround the implant relatively more tightly and act as a deflective height of contour. This height of contour helps to prevent food impaction and mechanical disruption of the hemi-desmosomal attachment of the soft tissue to the implant neck The body can be relatively square or tapered over a whole or a portion of the body region of the implant length.

The invention is further described with reference to the accompanying drawings.

DRAWINGS

FIG. 1a is a side-elevation view illustrating an embodiment of the dental implant of the present invention.

FIG. 1b is a cross-sectional view of a thread along line 1b—1b showing the positive rake angle of the spiral thread relative to bone.

FIG. 2 is a cross-sectional view taken along line 2—2 of FIG. 1.

DESCRIPTION

Figure 3:
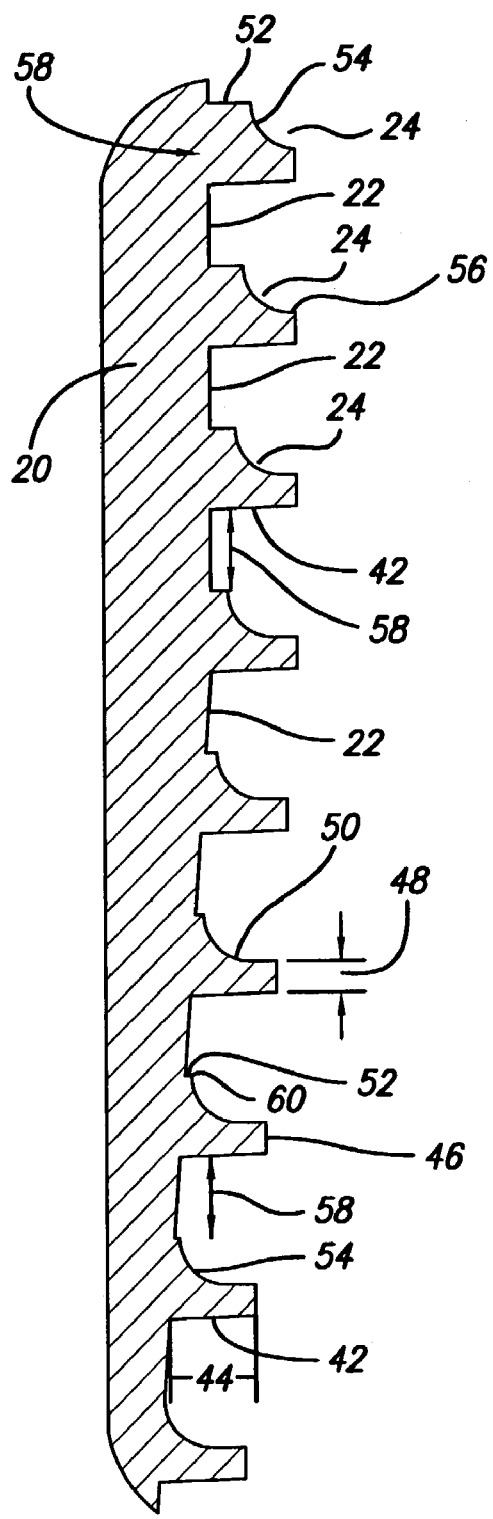
FIG. 3 is a partial sectional view taken from FIG. 2.

A dental implant has a threaded profile with a body; a coronal end of the body; an apical end of the body; a region on the body between the apical end and the coronal end. There is a helical thread extending along the region, the thread having an apical side and a coronal side and the depth of the apical side being substantially constant over the larger portion of the thread from the apical end to the coronal end of the implant. There are at least two cutting edges of the thread as the implant is threaded into a bone.

The threads have a depth being the distance between the body region and the outer edge of the thread. The edge of each thread has a depth which is substantially constant and provides a first cutting edge or surface. The interface between the first flat portion of the coronal side and the curved portion provides a second cutting edge or surface. The threads have a depth being the distance between the body region and the outer edge of the thread. The threads also have a width, the width being the distance between the apical end and the coronal end of each thread. Each thread ends in an edge and the width of each thread is substantially the same between the apical end and the coronal end of the implant.

There is a space between each thread, the space being the distance between the coronal end of a first thread and the apical end of an adjacent thread. The space is substantially the same between the majority of the threads in the implant.

The apical side is substantially flat between the body region and an extended position removed from the body region. The coronal side of the thread includes at least two distinct areas, at least one of the areas preferably being curved. The coronal side of the implant includes at least one flat portion and one curved portion.

The coronal side of some of the threads include a first flat portion adjacent to the body region, and a curved portion at the end remote from the first flat portion and a second flat portion between the curved portion and the edge of the thread. The threads end in an edge. The width of each thread edge is substantially the same between the apical end and the coronal end of the implant. The space between each thread is substantially the same. The depth of each thread of the implant is substantially the same.

There is an apical vent at the apical end of the implant, and a spiral vent extends axially along the length of the implant. The spiral vent extends about half way along the length of the dental implant, and the spiral vent extends about a quarter of the circumference of the implant. The spiral vent is reversed in direction relative to the thread direction whereby bone chips are urged downwardly in the spiral vent from the coronal end toward the apical end. Bone chips are urged towards the apical vent. The spiral vent has a positive rake angle.

The apical surface of the threads have an angle relative to the horizontal, the angle being about 3 degrees relative to the horizontal and wherein the horizontal is defined as perpendicular to the face of the body region.

An angled bevel area is located between the last thread adjacent to the coronal end and the coronal end of the implant. A concave shaped collar extending from the coronal end towards the coronal threads. As such the concave shaped collar extends from the coronal end, such concave shaped collar meeting an angled beveled end. The end of the angled beveled end remote from the collar interfaces with the body region of the implant. The body region of the implant extends towards the apical end, and the threads extending from a position towards the coronal end of the implant to a position toward the apical end of the implant.

The figures illustrates an embodiment of an implant 10. The implant 10 has a coronal end 12 and an apical end 14. The implant 10 has an apical vent or involution 16. There is a tapered portion 18 of the body region 20 and a relatively cylindrical portion 22 of the body region 20.

Directed from the tapered portion 18 and cylindrical portion 22 there is a series of helical threads 24 described in further detail below. The threads 24 do not start at the apical end but are removed somewhat from apical end, namely starting near or towards that end. The threads 24 likewise do not end at the coronal end 12 of the implant but are at a position somewhat removed from that end. In other embodiments the extent of the threads along the body region is different.

Between the coronal end 12 and the end the threads 24 near the coronal end 12, there is a concave shaped transmucosal polished collar 26 and between that collar and the threads 24 there is an angled bevel area of segment 28 which is of a wider depth than the thread portions 24. The concave transmucosal collar 26 allows circumferential gingival fibers to more tightly surround the implant and acts as a deflective height of contour. The angled bevel segment 28 has a tissue affinity surface to allow the hemidesmosomal attachment and sealing of the osteotomy. The angular segment is of wider depth than the threaded portion and this prevents inadvertent location of the implant 10 too deeply in the bone.

Directed from the apical end 16 to the coronal end, there is a spiral vent 30 which extends circumferentially about one-quarter of the circumference of the implant 10. The angle of the spiral vent 30 relative to the angle of the thread is such that it is about one quarter of the circumference from end 32 substantially adjacent to the apical end 14 to the end 34 substantially about half way up the length of the dental implant. As shown in FIG. 1, the helical threads 24 are directed upwardly from the left-hand side of the dental implant to the right hand side, thus permitting a clockwise turning of the implant into the bone. The spiral vent 30 extends contrarily from the right-hand side towards the left-hand side in a direction from its end 32 to 34. The length of the spiral vent, its depth and the amount it circumscribes the circumference of the dental implant can vary.

Figure 6:
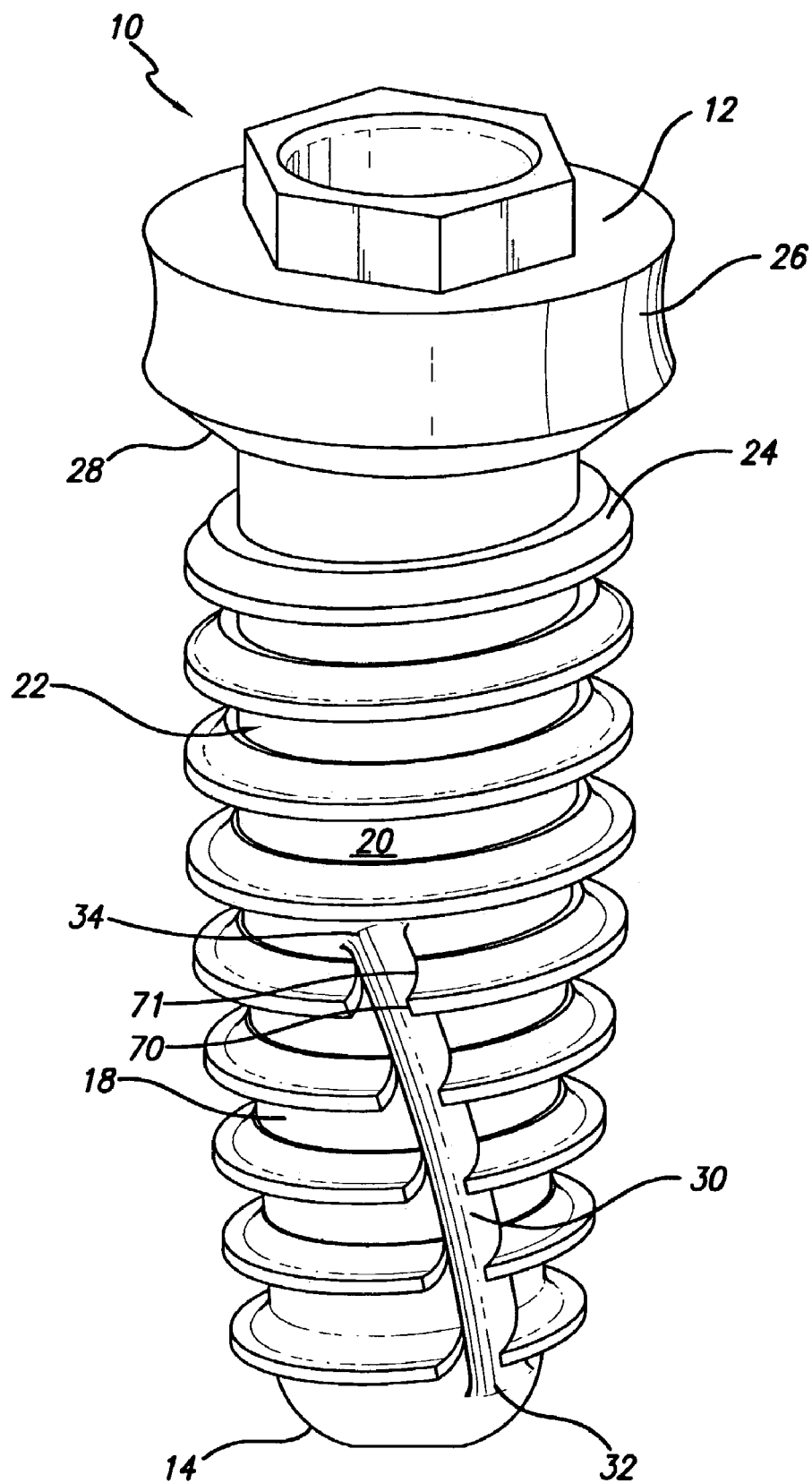
FIG. 6 is an isometric view illustrating a further embodiment of a dental implant of the present invention.

The edges of the threads 24 adjacent to the spiral vent 30 provide a positive rake angle for the vent thus permitting self-tapping of the vent. This configuration also permits bone chips to move downwardly as indicated by arrow 36 towards the outlet 32 and ultimately into the indentation 16 as the implant 10 is screwed into the bone. As such the spiral vent 30 is essentially reversed in its angulation relative to the axis 38 of the dental implant. With this configuration, the bone chips move downwardly along the line indicated by arrow 36 as the dental implant turns clockwise as indicated by arrow 40. This positive rake angle is reflected in the FIGS. 1a, 1b and 6 as a configuration where the tip edge 70 of the threads contact the bone in advance of the trailing surface 71 between the tip edge 70 and body region 20.

As shown in FIG. 3 there is a detail of the thread profile. This is represented relative to the body region 22. The depth 44 of each of the threads 24 is substantially the same for each thread as the threads move from the apical end to the coronal end of the implant. The depth of the apical edge 42 is substantially flat and constant in profile. Each thread 24 also has an edge 46, and the width defined by 48 of each edge is also substantially constant for each of the threads 24.

Each thread 24 also includes a coronal side generally indicated by numeral 50. The coronal side of each thread is formed by two or three segments as the case may be. Towards the apical end 16 there are three segments, an inner first flat segment 52, a radial segment 54 and connected therewith an outer second flat segment 56. The segment 52 adjacent to the body region 22 of the dental implant increases in depth between the apical end and the coronal end of the implant. The depth is the radially extending distance from the body region 20. The radial portion 54 is substantially of a constant radius and the remote second flat portion 56 of coronal side 50 of the thread decreases in radial length as the thread moves from the apical end 14 toward the coronal end 12 of the implant.

The final thread 24 closest to the coronal end 12 of the implant 10 is shown such that there is no outer coronal side remote portion 56. Also a feature of the invention is that in the final thread the segment 52 is about 50% of the depth 44

The spacing between each of the threads 24 as indicated by number 22 is of a constant distance as shown by arrows 58.

The interface, edge or surface 60 between the coronal edge 52 and the radial portion 54 acts as a second cutting edge for the implant. The first cutting edge, interface or surface is provided by the face 46 at the most extended portion of the dental implant.

The effect of this dual cutting thread is to provide a variable compression surface to the dental implant. As the length 52 increases in depth as the implant cross-section moves from the apical end to the coronal end, there is provided a configuration for the thread which enhances the operation of the implant.

The implant as such maintains stability in the bone by counterbalancing the reductive nature of the roughened surface as the implant turns through the bone. The implant itself maintains the dual cutting edge over its entire thread portion. This maintains inter-thread bone without compromising stability. Moreover, there is a reduction in the compression of interthread bone which would otherwise lead to microfracture and decrease the bone strength. As such, therefore, the dual cutting thread with the variable compression surface has effective advantages in a dental implant configuration.

Figure 5:
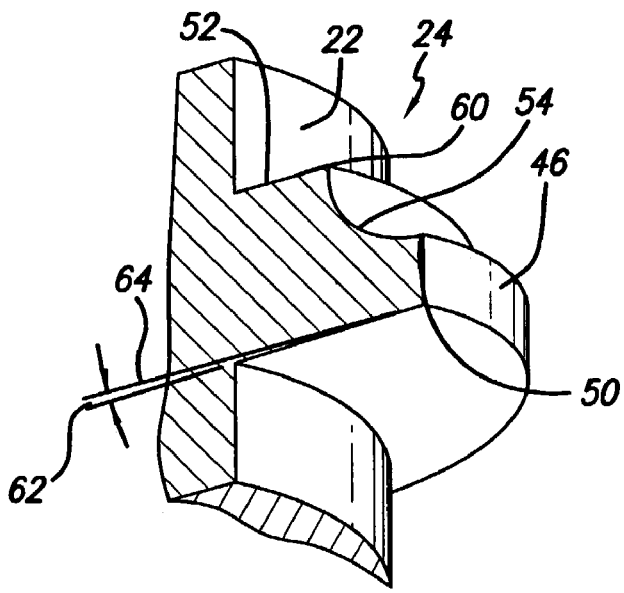
FIG. 5 is a partial sectional view is a partial sectional view of a thread and the body region adjacent the coronal end.
Figure 4:
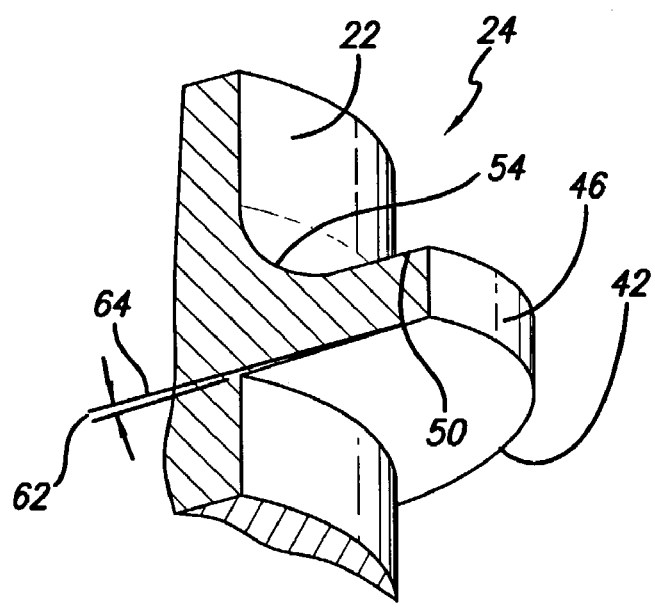
FIG. 4 is a partial sectional view of a thread and the body region adjacent the apical end.

As often shown in the isometric views of FIGS. 4 and 5 detailing the thread the apical side 42 of the thread 24 is provided with a three degree rise 62 relative to the horizontal line 64. The coronal side 52 is substantially horizontal.

An operation implant can be placed into a predrilled osteotomy site that either matches the external depth of the implant body common name meaning that is the narrowest depth between the threads or into a site that is narrower than the external depth of the implant. Placing the implant into a narrower site will provide additional bone compression and therefore greater initial stability.

The embodiment of the present invention provides unique advantages in providing a dental implant fixture with a tapered and cylindrical profile and a unique external thread profile that offers superior stability when it is implanted in the bone.

The stability of the implant is such that essentially earlier or immediate loading of the implant will be possible, thereby minimizing the distress and time involved in implantation of the dental implant and its becoming operative in that patient.

Figure 7:
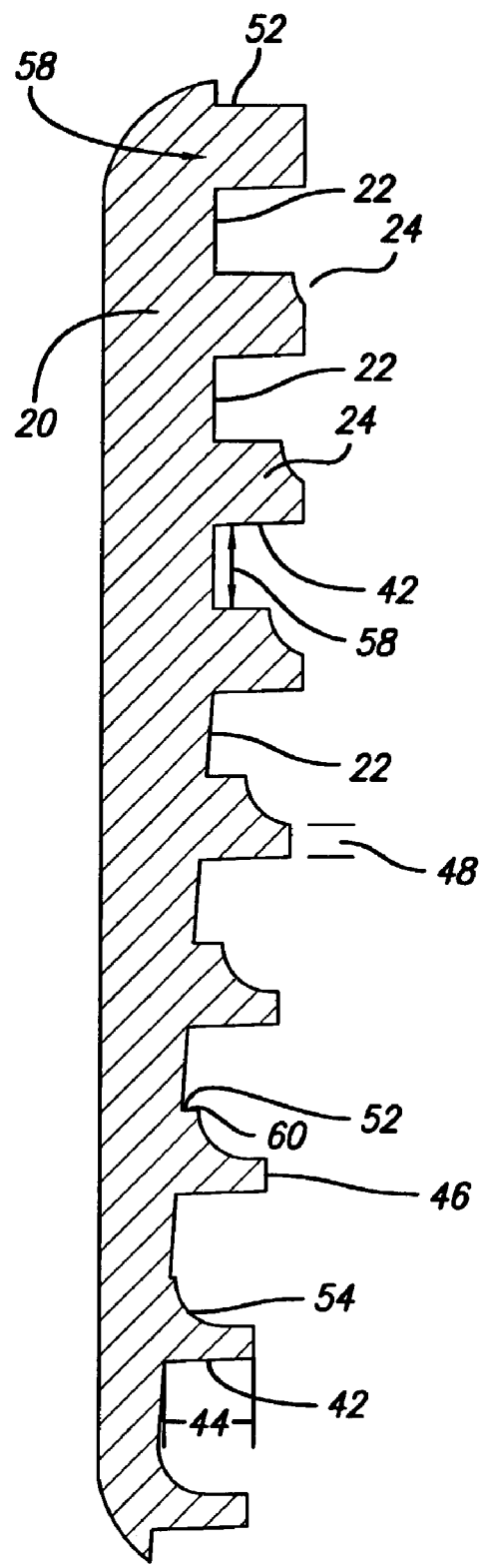
FIG. 7 is an alternative embodiment of a partial sectional view similar to FIG. 3, and showing a different thread profile.
Figure 8:
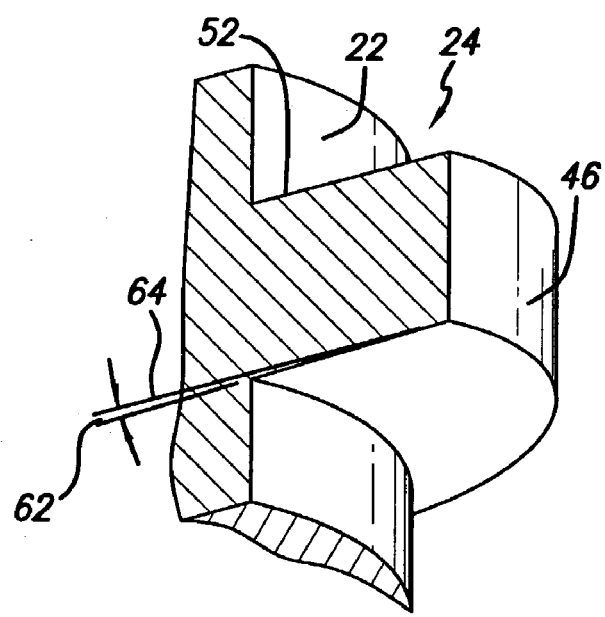
FIG. 8 is a partial sectional view is a partial sectional view of a final thread and the body region adjacent the coronal end for the embodiment of FIG. 7

In the embodiment illustrated in FIGS. 7 and 8 there is shown an embodiment where the final thread 24 closest to the coronal end 12 of the implant 10 is such that the segment 52 is about 100% of the depth 44 In this case there is no flat remote portion segment 56. In other iterations of the invention the segment 52 can be a different amount of the percentage of the depth 44 as the final thread. Many other forms of the invention exist, each different from the other in that detail only. For instance, instead of a roughened surface, it is possible that a smooth surface or bioactive coating may be used for the implant. Additionally, one or more side vents can be used in the implant.

In yet a further form of the invention, the thread towards the coronal end may still retain a portion of the second flat part of the coronal edge of the thread. As such it may not be a two portion segment of coronal side of the thread. In yet other forms of the invention the implant may be formed totally on a cylindrical body, or totally on a tapered body or on different combinations of taper and cylindrical cross-section. Although the coronal thread side has two flat portions, they may be relatively angled in relation to each other and be at different angles relative to he body region Although the invention has been described with reference to different embodiments, it will be appreciated that a wide range of modifications are possible. Some features of the invention may be used without other features. The invention is to be determined and construed broadly in a manner consistent with the embodiments and with the following claims.

What is claimed is:

1. A dental implant having a threaded profile comprising
   a) a body;
   b) a coronal end of the body;
   c) an apical end of the body;
   d) a region on the body between the apical end and the coronal end; and
   e) a helical thread extending along the region, the thread having an apical side and a coronal side, wherein the coronal side of the thread includes at least two distinct areas the three having a depth, the depth being the distance between the body region and the outer edge of the thread and the depth of the apical side being substantially constant over the larger portion of the thread from the apical end to the coronal end of the implant and there being at least two cutting edges in at least some of the threads, the cutting edges being for inter engagement with bone as the implant is threaded into the bone.

2. A dental implant as claimed in claim 1 wherein the apical side is substantially flat between the body region and an extended position removed from the body region.

3. A dental implant as claimed in claim 1 wherein the coronal side of the implant includes at least one flat portion and one curved portion.

4. A dental implant as claimed in claim 3 wherein the coronal side of the thread includes a first flat portion adjacent to the body region, and a curved portion at the end remote from the first flat portion and, in at least some of the threads, there being a second flat portion between the curved portion and the edge of the thread.

5. A dental implant as claimed in claim 1 wherein the threads have a width, the width being the distance between the apical end and the coronal end of each thread, the wherein each thread ends in an edge and wherein the width of each thread is substantially the same between the apical end and the coronal end of the implant.

6. A dental implant as claimed in claim 1 wherein there is a space between each thread, the space being the distance between the coronal end of a first thread and the apical end of an adjacent thread, and wherein the space is substantially the same between the majority of the threads in the implant.

7. A dental implant as claimed in claim 1 wherein the depth of each thread of the implant is substantially the same.

8. A dental implant as claimed in claim 1 wherein the depth of the apical side of each thread is substantially the same.

9. A dental implant as claimed in claim 1 including an apical vent at the apical end of the implant.

10. A dental implant as claimed in claim 1 including a spiral vent extending axially along the length of the implant.

11. A dental implant as claimed in claim 10 wherein the spiral vent extends about half way along the length of the dental implant.

12. An implant as claimed in claim 10 wherein the spiral vent extends about a quarter of the circumference of the implant.

13. An implant as claimed in claim 10 wherein the spiral vent is reversed in direction relative to the thread direction whereby bone chips are urged downwardly in the spiral vent from the coronal end toward the apical end, and wherein such bone chips are urged towards the apical vent.

14. A dental implant as claimed in claim 10 wherein the spiral vent has a positive rake angle.

15. An implant as claimed in claim 1 wherein the apical surface of the thread has an angle relative to a horizontal, the angle being about 3 degrees relative to the horizontal, and wherein the horizontal is defined as perpendicular to the face of the body region.

16. An implant as claimed in claim 1 including an angled bevel area between the last thread adjacent to the coronal end and the coronal end of the implant.

17. An implant as claimed in claim 1 including a concave shaped collar extending from the coronal end towards the coronal threads.

18. An implant as claimed in claim 1 including a concave shaped collar extending from the coronal end, such concave shaped collar meeting an angled beveled end and the end of the angled beveled end remote from the collar and interfacing with the body region of the implant, and the body region of the implant extending towards the apical end, and the threads extending from a position towards the coronal end of the implant to a position toward the apical end of the implant.

19. A dental implant having a threaded profile comprising:
   a) a body;
   b) a coronal end of the body;
   c) an apical end of the body;
   d) a region on the body between the apical end and the coronal end; and
   e) a helical thread extending along the region, the thread having an apical side and a coronal side and a depth, the depth being the distance between the body region and the outer edge of the thread, the depth of the apical side being substantially constant over the larger portion of the thread from the apical end to the coronal end of the implant, the apical side being substantially flat between the body region and an extended position removed from the body region, and wherein the coronal side of the thread includes at least one flat portion and one curved portion.

20. A dental implant as claimed in claim 19 where the coronal side of the thread includes at least two distinct areas.

21. A dental implant as claimed in claim 19 wherein the coronal side of the thread includes a first flat portion adjacent to the body region, and a curved portion at the end remote from the first flat portion and a second flat portion between the curved portion and the edge of the thread.

22. A dental implant as claimed in claim 19 wherein the threads have a width, the width being the distance between the apical end and the coronal end of each thread, the wherein each thread ends in an edge end wherein the width of each thread is substantially the same between the apical end and the coronal end of the implant.

23. A dental implant as claimed in claim 19 wherein there is a space between each thread, the space being the distance between the coronal end of a first thread and the apical end of an adjacent thread, and wherein the space is substantially between the majority of the threads in the implant.

24. A dental implant as claimed in claim 19 wherein the depth of each thread of the implant is substantially the same.

25. A dental implant as claimed in claim 19 wherein the depth of the apical side of each thread is substantially the same.

26. A dental implant as claimed in claim 19 including an apical vent at the apical end of the implant.

27. A dental implant as claimed in claim 19 including a spiral vent extending axially along the length of the implant.

28. A dental implant as claimed in claim 19 wherein the spiral vent extends about half way along the length of the dental implant.

29. An implant as claimed in claim 27 wherein the spiral vent extends about a quarter of the circumference of the implant.

30. An implant as claimed in claim 27 wherein the spiral vent is reversed in direction relative to the thread direction whereby bone chips are urged downwardly in the spiral vent from the coronal end toward the apical end, and wherein such bone chips are urged towards the apical vent.

31. A dental implant as claimed in claim 27 wherein the spiral vent has a positive rake angle.

32. An implant as claimed in claim 19 wherein the apical surface of the thread has an angle relative to the horizontal, the angle being about 3 degrees relative to the horizontal and wherein the horizontal is defined as perpendicular to the face of the body region.

33. An implant as claimed in claim 19 including an angled bevel area between the last thread adjacent to the coronal end and the coronal end of the implant.

34. A dental implant having a threaded profile comprising
a) a body;
b) a coronal end of the body;
c) an apical end of the body;
d) a region on the body between the apical end and the coronal end; and
e) an helical thread extending along the region, the thread having an apical side and a coronal side and the depth of the apical side being substantially constant over the larger portion of the thread from the apical end to the coronal end of the implant, the coronal side of the thread includes at least two distinct areas.

35. A dental implant as claimed in claim 34 wherein the coronal side of the thread includes at least one flat portion and one curved portion.

36. A dental implant as claimed in claim 34 wherein the coronal side of the thread includes a first flat portion adjacent to the body region, and a curved portion at the end remote from the first flat portion and a second flat portion between the curved portion and the edge of the thread.

37. A dental implant as claimed in claim 34 wherein the threads have a width, the width being the distance between the apical end and the coronal end of each thread, the wherein each thread ends in an edge and wherein the width of each thread is substantially the same between the apical end and the coronal end of the implant.

38. A dental implant as claimed in claim 34 wherein there is a space between each thread, the space being the distance between the coronal end of a first thread and the apical end of an adjacent thread, and wherein the space is substantially between the majority of the threads in the implant.

39. A dental implant as claimed in claim 34 wherein the depth of the apical side of each thread is substantially the same.

40. A dental implant as claimed in claim 34 including an apical vent the apical end of the implant.

41. A dental implant as claimed in claim 34 including a spiral vent extending axially along the length of the implant.

42. A dental implant as claimed in claim 34 wherein the spiral vent extends about half way along the length of the dental implant.

43. An implant as claimed in claim 42 wherein the spiral vent extends about a quarter of the circumference of the implant.

44. An implant as claimed in claim 42 wherein the spiral vent is reversed in direction relative to the thread direction whereby bone chips are urged downwardly in the spiral vent from the coronal end toward the apical end, and wherein such bone chips are urged towards the apical vent.

45. A dental implant as claimed in claim 42 wherein the spiral vent has a positive rake angle.

46. An implant as claimed in claim 34 wherein the apical surface of the thread has an angle relative to the horizontal, the angle being about 3 degrees relative to the horizontal and wherein the horizontal is defined as perpendicular to the face of the body region.

47. An implant as claimed in claim 34 including an angled bevel area between the last thread adjacent to the coronal end and the coronal end of the implant.

48. A dental implant having a threaded profile comprising:
a) a body;
b) a coronal end of the body;
c) an apical end of the body;
d) a region on the body between the apical end and the coronal end; and
e) a helical thread extending along the region, the thread having an apical side and a coronal side and the depth of the apical side being substantially constant over the larger portion of the thread from the apical end to the coronal end of the implant, the threads ending in an edge and wherein the width of each thread edge is substantially the same between the apical end and the coronal end of the implant, and wherein there is a space between each thread, the space being the distance between the coronal end of a first thread and the apical end of an adjacent thread, wherein the space is substantially between the majority of the threads in the implant, and wherein the coronal side of the thread includes at least one flat portion and one curved portion.

49. A dental implant as claimed in claim 48 wherein the coronal side of the thread includes a first flat portion adjacent to the body region, and a curved portion at the end remote from the first flat portion and a second flat portion between the curved portion and the edge of the thread.

50. A dental implant as claimed in claim 48 wherein the depth of the apical side of each tread is substantially the same.

51. A dental implant as claimed in claim 48 including an apical vent at the apical end of the implant.

52. A dental implant as claimed in claim 48 including a spiral vent extending axially along the length of the implant, the spiral vent extending about half way along the length of the dental implant, and extending about a quarter of the circumference of the implant.

53. An implant as claimed in claim 48 wherein the spiral vent is reversed in direction relative to the thread direction whereby bone chips are urged downwardly in the spiral vent from the coronal end toward the apical end, and wherein such bone chips are urged towards the apical vent.

54. A dental implant as claimed in claim 53 wherein the spiral vent has a positive rake angle.

55. A dental implant having a threaded profile comprising
a) a body;
b) a coronal end of the body wherein the coronal side of the thread includes at least one flat portion and one curved portion;
c) an apical end of the body;
d) a region on the body between the apical end and the coronal end;
e) a helical thread extending along the region, the thread having an apical side and a coronal side and the depth of the apical side being substantially constant over the larger portion of the thread from the apical end to the coronal end of the implant, and
f) a spiral vent extending axially along the length of the implant, the spiral vent extending in a reverse direction relative to the thread direction whereby bone chips are urged downwardly in the spiral vent from the coronal end toward the apical end.

56. A dental implant as claimed in claim 55 wherein the coronal side of the thread includes a first flat portion adjacent to the body region, and a curved portion at the end remote from the first flat portion and a second flat portion between the curved portion and the edge of the thread.

57. A dental implant as claimed in claim 55 wherein the depth of the apical side of each thread is substantially the same.

58. A dental implant as claimed in claim 55 including an apical vent at the apical end of the implant.

59. A dental implant as claimed in claim 53 wherein the spiral vent has a positive rake angle.

60. A dental implant as claimed in claim 4 wherein the final thread near or adjacent to the coronal end is such that the first flat portion occupies about 50% of the overall depth of the thread.

61. A dental implant as claimed in claim 4 wherein the final thread near or adjacent to the coronal end is such that the first flat portion occupies about 100% of the overall depth of the thread.

62. A dental implant as claimed in claim 19 wherein the final thread near or adjacent to the coronal end is such that the first flat portion occupies about 50% of the overall depth of the thread.

63. A dental implant as claimed in claim 19 wherein the final thread near or adjacent to the coronal end is such that the first flat portion occupies about 100% of the overall depth of the thread.

64. A dental implant as claimed in claim 37 wherein the final thread near or adjacent to the coronal end is such that the first flat portion occupies about 50% of the overall depth of the thread.

65. A dental implant as claimed in claim 37 wherein the final thread near or adjacent to the coronal end is such that the first flat portion occupies about 100% of the overall depth of the thread.

66. A dental implant as claimed in claim 50 wherein the final thread near or adjacent to the coronal end is such that the first flat portion occupies about 50% of the overall depth of the thread.

67. A dental implant as claimed in claim 50 wherein the final thread near or adjacent to the coronal end is such that the first flat portion occupies about 100% of the overall depth of the thread.

68. A dental implant as claimed in claim 57 wherein the final thread near or adjacent to the coronal end is such that the first fist portion occupies about 50% of the overall depth of the thread.

69. A dental implant as claimed in claim 57 wherein the final thread near or adjacent to the coronal end is such that the first flat portion occupies about 100% of the overall depth of the thread.

70. A dental implant as claimed in claim 3 wherein at least one of the said distinct areas is substantially curved.

71. A dental implant as claimed in claim 20 wherein at least one of the said distinct areas is substantially curved.

72. A dental implant as claimed in claim 34 wherein at least one of the said distinct areas is substantially curved.

* * * * *